United States Patent [19]

Lehr et al.

[11] Patent Number: 4,812,453

[45] Date of Patent: Mar. 14, 1989

[54] USE OF 1-BENZYL-AMINOALKYL-PYRROLIDI-NONES AS ANTIDEPRESSANTS

[75] Inventors: Erich Lehr, Waldalgesheim; Wolf-Dietrich Bechtel, Appenheim; Karin Boke-Kuhn, Gau-Algesheim; Claus Schneider, Ingelheim am Rhein; Gerhard Walther, Bingen; Karl-Heinz Weber, Gau-Algesheim, all of Fed. Rep. of Germany

[73] Assignee: Boehringer Ingelheim KG, Ingelheim am Rhein, Fed. Rep. of Germany

[21] Appl. No.: 102,074

[22] Filed: Sep. 29, 1987

[30] Foreign Application Priority Data

Oct. 8, 1986 [DE] Fed. Rep. of Germany ....... 3634220

[51] Int. Cl.$^4$ ............................................ A61K 31/495
[52] U.S. Cl. ...................................................... 514/255
[58] Field of Search ......................................... 514/255

[56] References Cited

PUBLICATIONS

Chem. Abst., 103-37365u (1985).

*Primary Examiner*—Stanley J. Friedman
*Attorney, Agent, or Firm*—David E. Frankhouser; Alan P. Stempel; Mary-Ellen M. Timbers

[57] ABSTRACT

The invention relates to the use of 1-benzyl-aminoalkyl-pyrrolidinones as antidepressants.

1 Claim, No Drawings

USE OF 1-BENZYL-AMINOALKYL-PYRROLIDINONES AS ANTIDEPRESSANTS

The invention relates to the use of 1-benzyl-aminoalkyl-pyrrolidinones of general formula

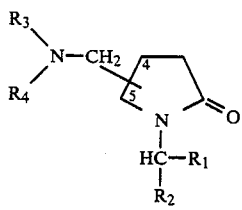

wherein $R_1$ represents hydrogen or an alkyl group, $R_2$ represents a phenyl group which may be mono- or disubstituted by alkoxy, fluorine, chlorine, bromine, trifluoromethyl, alkyl, hydroxy or nitro, or $R_2$ represents a pyridyl group, $R_3$ represents hydrogen or an alkyl group and $R_4$ may represent hydrogen or an alkyl group or the two groups $R_3$ and $R_4$ together with the nitrogen atom may represent a saturated 5- or 6-membered ring which may contain an O or N atom as a further heteroatom and may optionally be substituted by methyl or they may form an imidazole ring, wherein the aminoalkyl group is in the 4 or 5 position, and the pharmacologically acceptable acid addition salts thereof, as antidepressants.

In general formula I the term "alkyl" indicates a straight chained or branched alkyl group with 1 to 4 carbon atoms such as, for example, methyl, ethyl, propyl, isopropyl, n-butyl or tert.-butyl and the term "alkoxy" indicates a group with 1 to 2 carbon atoms; the pyridyl ring given as a definition of $R_2$ may be linked to the methylene bridge in the 2, 3 or 4 position. Methyl and ethyl are the preferred alkyl groups.

Compounds of general formula I and processes for preparing them are known from European Patent Application No. 136 658, which discloses the efficacy of the compounds in cases of restricted cerebral performance.

Surprisingly, it has been found that the compounds of general formula I are highly effective antidepressants of a new structural type.

Preferred compounds are the compounds of general formula I wherein $R_1$ represents hydrogen, $R_2$ represents a phenyl group optionally substituted by fluorine, chlorine, methyl or methoxy in the o or p position and $R_3$ and $R_4$ represent hydrogen or methyl or $R_3$ and $R_4$ together represent morpholine or N-methylpiperazine.

Other suitable compounds include:
1-(3,4-Dimethoxybenzyl)-4-aminomethyl-pyrrolidin-2-one
1-(4-Methylbenzyl)-4-aminomethyl-pyrrolidin-2-one
1-(3-Trifluoromethylbenzyl)-4-aminomethyl-pyrrolidin-2-one
1-(α-Methylbenzyl)-4-aminomethyl-pyrrolidin-2-one
1-Benzyl-4-piperidinomethyl-pyrrolidin-2-one
1-Benzyl-4-(N-methylpiperazinomethyl)-pyrrolidin-2-one
1-Benzyl-4-(imidazo-1-yl-methyl)-pyrrolidin-2-one
1-Benzyl-4-methylaminomethyl-pyrrolidin-2-one
1-(p-Fluorobenzyl)-4-dimethylaminomethyl-pyrrolidin-2-one
1-(4-Nitrobenzyl)-4-aminomethyl-pyrrolidin-2-one
1-(4-Hydroxybenzyl)-4-aminomethyl-pyrrolidin-2-one
1-(o-Chlorobenzyl)-4-aminomethyl-pyrrolidin-2-one
1-(o-Chlorobenzyl)-4-diethylaminomethyl-pyrrolidin-2-one
1-Benzyl-4-isopropylaminomethyl-pyrrolidin-2-one
1-(p-Methylbenzyl)-4-diethylaminomethyl-pyrrolidin-2-one
1-Benzyl-5-dimethylaminomethyl-pyrrolidin-2-one
1-Benzyl-5-morpholinomethyl-pyrrolidin-2-one
1-Benzyl-5-(4-methylpiperazino)-methyl-pyrrolidin-2-one
1-(4-Methylbenzyl)-5-dimethylaminomethyl-pyrrolidin-2-one
1-(4-Methylbenzyl)-5-diethylaminomethyl-pyrrolidin-2-one
1-(p-Chlorobenzyl)-5-diethylaminomethyl-pyrrolidin-2-one
1-(3,4-Dichlorobenzyl)-5-dimethylaminomethyl-pyrrolidin-2-one
1-(3,4-Dichlorobenzyl)-5-diethylaminomethyl-pyrrolidin-2-one
1-(p-Methoxybenzyl)-5-dimethylaminomethyl-pyrrolidin-2-one
1-(p-Methoxybenzyl)-5-diethylaminomethyl-pyrrolidin-2-one and
1-Benzyl-5-aminomethyl-pyrrolidin-2-one.

Preferred compounds are:
1-(4-Methoxybenzyl)-4-aminomethyl-pyrrolidin-2-one
1-Benzyl-4-N,N-diethylaminomethyl-pyrrolidin-2-one
1-(4-Fluorobenzyl)-4-aminomethyl-pyrrolidin-2-one
1-(4-Chlorobenzyl)-4-aminomethyl-pyrrolidin-2-one
1-(4-Pyridylmethyl)-4-aminomethyl-pyrrolidin-2-one
1-(4-Fluorobenzyl)-4-(morpholinomethyl)-pyrrolidin-2-one
1-Benzyl-4-(N-methylpiperazinylmethyl)-pyrrolidin-2-one and
1-Benzyl-4-methylaminomethyl-pyrrolidin-2-one.

Particularly preferred compounds are:
1-Benzyl-4-aminomethyl-pyrrolidin-2-one
1-Benzyl-5-pyrrolidinomethyl-pyrrolidin-2-one
1-Benzyl-5-diethylaminomethyl-pyrrolidin-2-one and
1-(p-chlorobenzyl)-5-dimethylaminomethyl-pyrrolidin-2-one.

A sensitive test for preclinical demonstration of antidepressant properties is the chick call test. The call frequency of isolated one-day-old chicks which decreases during the course of the test is taken as an experimental behavioural model for manifestations of resignation in depression. The method was validated by testing numerous neurotropically active substances; it is characterised by highly reproducible selectivity for antidepressants which are already clinically tried and tested and which are capable of reactivating the lowered call rate, as a function of dosage (distress call activation in isolated chicks; A new behavioural model for antidepressants, E. Lehr, Psychopharmacol. 89. 21 (1986); Activierung des Kontaktrufens als tierexperimentelles Verhaltensmodell zur Depressionsforschung, [Activation of contact calling as an experimental behavioural model for researching depression], E. Lehr, Fortschr. Neurol. Psychiat. 54, 26 (1986).

Table I gives the pharmacological data for 1-benzyl-4-aminomethyl-pyrrolidin-2-one (fumarate) [Compound A]. By comparison the corresponding values for 1-acetamido-2-pyrrolidinone [Compound B], a structurally similar nootropic, are also given.

TABLE 1

|  | Compound A | Compound B |
|---|---|---|
| Chick call test ED$_{150}$, mg/kg i.p. | 40 | >>160 |
| Tetrabenazine antagonism (ptosis alleviation, mouse) | 110 | >>640 |
| LD$_{50}$, mouse mg/kg by oral route | >>2000 |  |
| Effect on cholinergic function | Demand | none |
| Receptor bonding (adrenergic, serotonergic) | none | none |
| IC$_{50}$ [$10^{-9}$ mol/ltr] | >10 000 |  |

Table II gives the pharmacological data of the above mentioned chick call test of some compounds of the invention.

TABLE II $$\text{R}\underset{\underset{\text{CH}_2-\text{R}_2}{|}}{\overset{}{\underset{\text{N}}{\diagdown}}}\text{=O} \quad \text{I}$$

HCl or Fu

|  | R$_2$ | Chick call test ED$_{150}$ i.p. mg/kg |
|---|---|---|
| R(4-position) | | |
| C —CH$_2$—NH$_2$ | —C$_6$H$_4$—OCH$_3$ | 25 |
| D —CH$_2$—NH$_2$ | —C$_6$H$_4$—F | 20 |
| E —CH$_2$—NH$_2$ | pyridyl | 100 |
| F —CH$_2$—NH$_2$ | —C$_6$H$_4$—Cl | 10 |
| G —CH$_2$—N(morpholino) | —C$_6$H$_4$—F | 80 |
| H —CH$_2$—N(4-methylpiperazinyl) | —C$_6$H$_5$ | 18 |
| R(5-position) | | |
| J —CH$_2$—N(C$_2$H$_5$)$_2$ | —C$_6$H$_5$ | 0.01 |

TABLE II-continued $$\text{R}\underset{\underset{\text{CH}_2-\text{R}_2}{|}}{\overset{}{\underset{\text{N}}{\diagdown}}}\text{=O} \quad \text{I}$$

HCl or Fu

|  | R$_2$ | Chick call test ED$_{150}$ i.p. mg/kg |
|---|---|---|
| K —CH$_2$—N(pyrrolidinyl) | —C$_6$H$_5$ | 0.1 |
| L —CH$_2$—N(CH$_3$)$_2$ | —C$_6$H$_4$—Cl | 0.1 |

On the basis of the data shown, there is clear evidence of preclinically antidepressant properties, whilst the compounds according to the invention do not show the typical side effects of conventional antidepressants, such as sedation. The absence of receptor bonding properties and/or inhibition of resorption of biogenic amines indicates a completely new mechanism of activity for compounds with an antidepressant effect. The cholinomimetic property of the compounds of general formula I rules out any cardiotoxicity, which is caused in conventional antidepressants by their anticholinergic side effects and is one of the most serious undesirable drawbacks of such drugs. Owing to the cholinergic property of the compounds of general formula I it is possible to use the compounds in cases of depression even in geriatric patients in whom, owing to their cholinergic malfunction, conventional antidepressants are contraindicated on account of their anticholinergic side effects.

Processes for preparing compounds of general formula I and the pharmacologically acceptable acid addition salts thereof are described in European Patent Application No. 136 658, the contents of which are referred to here.

The compounds of general formula I may be used on their own or in conjunction with other active substances according to the invention, and possibly in conjunction with other pharmacologically active substances. Suitable forms for administration include tablets, capsules, suppositories, solutions, syrups, emulsions and dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release, such as carboxypolymethylene, carboxymethylcellulose, cellulose acetate phthalate or polyvinyl acetate. The tablets may also consist of several layers.

Coated tablets may be prepared in the same way by coating cores produced analogously to the tablets with subtances conventionally used for tablet coatings, e.g. collidone or shellack, gum arabic, talc, titanium dioxide or sugar. In order to obtain delayed release or avoid intolerance, the core may also consist of several layers. Similarly, the tablet coating may also consist of several layers in order to obtain delayed release, and the excipients mentioned for the tablets may be used.

Syrups containing the active substances or combinations of active substances according to the invention may additionally contain a sweetener such as saccharin, cyclamate, glycerol or sugar and a flavour-enhancing agent, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such a p-hydroxybenzoates.

Injection solutions are produced in the usual way, e.g. by adding preservatives such as p-hydroxybenzoates or stabilisers such as alkali metal salts or ethylene diamine tetraacetic acid and the solutions are transferred into injection vials of ampoules.

Capsules containing one or more active substances or combinations of active substances may be produced, for example, by mixing the active substances with inert carriers such as lactose or sorbitol and sealing the mixture in gelatine capsules. Suitable suppositories may be produced, for example, by mixing with the carriers provided for this purpose, such as neutral fats or polyethylene glycol or the derivatives thereof.

The therapeutically effective dosage is generally from 1 to 150 mg, preferably from 50 to 100 mg for each single dose.

The Examples which follow illustrate the invention without restricting its scope:

EXAMPLE 1

1-Benzyl-4-aminomethyl-pyrrolidin-2-one 54 g (0.16 mol) of 4-phthalimidomethyl-1-benzyl-pyrrolidin-2-one are stirred into 1.3 liters of ethyl alcohol after the addition of 32 g of hydrazine hydrate for 4 hours at ambient temperature. The precipitate (phthalic acid hydrazide) is suction filtered and the filtrate is concentrated by evaporation. 500 ml of methylene chloride are added to the residue and it is extracted three times with 100 ml of water. The organic phase is dried and evaporated. The residue remaining is dissolved in 500 ml of methanol and 20 g (0.17 mol) of solid fumaric acid are added in batches at boiling temperature with stirring. When the mixture cools, colourless crystals are precipitated which are suction filtered and then washed with methanol and ether. Yield: 20–25 g (48–60% of theory), m.p. 209°–211° C.

The compound contains ½ mol of fumaric acid. The starting material is obtained as follows:

(a) 94 g (0.46 mol) of 1-benzyl-4-hydroxymethyl-pyrrolidin-2-one are stirred with 700 ml of methylene chloride and 40 ml (0.54 mol) of thionylchloride for 25 hours while refluxing and the reaction mixture is then neutralised with dilute ammonia whilst being cooled. After separation, drying and evaporation, 85–90 g of a dark oil are left behind, which is used directly for further reaction.

(b) 43.5 g (0.195 mol) of crude 1-benzyl-4-chloromethyl-pyrrolidin-2-one, 36 g (0.195 mol) of phthalimide potassium and 700 ml of dimethylformamide are refluxed for 2 hours. The reaction mixture is then evaporated in vacuo and the residue is taken up in methylene chloride. It is extracted several times with water, the organic phase is dried and after chromatography on SiO₂ 45 g (70% of theory) of the phthalimido compound are obtained, m.p. 108°–109° C.

EXAMPLE 2

1-Benzyl-4-aminomethyl-pyrrolidin-2-one (a) 58 g (0.29 mol) of 1-benzyl-4-nitrilo-pyrrolidin-2-one are dissolved in methanol and catalytically hydrogenated with the addition of liquid ammonia over Raney nickel. After the reaction solution has been concentrated by evaporation, it is dissolved in methanol, the residual catalyst is filtered off and after the filtrate has been heated to about 50° C. it is mixed with 17 g of fumaric acid. The fumaric acid briefly goes into solution when stirred, then the crystallization of the 1-benzyl-4-aminomethyl-pyrrolidin-2-one fumarate begins.

Yield: 68 g (=91% of theory); m.p. 192°–194° C.

(b) The nitrilo compound is obtained in a 96% yield in the form of an oil from the corresponding amide, m.p. 162°–166° C., by dehydration using $POCl_3$ in dimethylformamide at about 60° C.

EXAMPLE 3

Racemate cleaving of 1-Benzyl-4-aminomethyl-pyrrolidin-2-one (a) 24.0 g (0.117 mol) of 1-benzyl-4-aminomethyl-pyrrolidin-2-one are dissolved in 200 ml of hot methanol and 17.6 g (0.117 mol) of L(+)-tartaric acid are also dissolved in 200 ml of hot methanol. The two solutions are combined and cooled to ambient temperature with stirring, whereupon the salt crystallizes out. The crystals are suction filtered while cold, washed with cold methanol and dried.

Yield: 18.0 g of 4-aminomethyl-1-benzyl-pyrrolidin-2-one tartrate, m.p. 204°–206° C. (from methanol), $\alpha_D = +6.3°$ (c=1.0; water).

(b) In order to convert the tartrate into the base the tartrate is dissolved cold in 20 ml of water and 10 ml of concentrated sodium hydroxide solution and extracted three times with methylene chloride, then the combined mehtylene chloride phases are dried over $MgSO_4$ and the solvent is eliminated in vacuo. The (−)-4-aminomethyl-1-benzyl-pyrrolidin-2-one is obtained, $\alpha_D = -8.4°$ (c=1.0; water).

(c) The mother liquors obtained in the processing described in (a) are concentrated by evaporation in vacuo. 38.0 g of the tartrate is obtained, which is taken up cold in 140 ml of water and 50 ml of concentrated sodium hydroxide solution and extracted three times with methylene chloride. The combined methylene chloride phases are dried over $MgSO_4$ and the solvent is eliminated in vacuo. 19.3 g of base are obtained, which is converted into the corresponding tartrate with D-(−)-tartaric acid as described in (a). Yield: 19.0 g m.p. 204°–205° C.

(d) The conversion of the tartrate into the base is carried out as described in (b). 5.7 g of (+)-4-aminomethyl-1-benzyl-pyrrolidin-2-one are obtained with a rotation $\alpha_D = +8.4°$ (c=1.0; water).

EXAMPLE 4

(−)-1-Benzyl-4-dimethylaminomethyl-pyrrolidin-2-one 4.0 g (0.02 mol) of (−)-1-benzyl-4-aminomethyl-pyrrolidin-2-one and 5.4 g of 85% formic acid are mixed with 4.8 ml of formalin solution and stirred overnight at 100° C. (oil bath). Then the excess acid is distilled off in vacuo and the residue is taken up in water, made alkaline with concentrated sodium hydroxide solution and extracted three times with methylene chloride. The combined methylene chloride phases are washed with water, dried over sodium sulphate, the solvent is concentrated in vacuo and the residue is filtered over an SiO$_2$ column (eluant: methylene chloride:methanol=97:3). The uniform fraction is concentrated by evaporation in vacuo. The title compound is obtained in a yield of 3.5 g (in the form of an oil). $\alpha_D = -7.6°$ (c=1.0; methanol) $\alpha_D = -16.8°$ (c=1.0; water).

Analogously to Example 4, 6.1 g of (+)-1-benzyl-4-dimethylaminomethyl-pyrrolidin-2-one are obtained, $\alpha_D = +7.9°$ (c=1.0; methanol), from 5.8 g (0.028 mol) of (+)-1-benzyl-4-aminomethyl-pyrrolidin-2-one 7.9 g of 85% formic acid and 7 ml of formalin solution.

EXAMPLE 5

1-Benzyl-4-di-ethylaminomethyl-pyrrolidin-2-one 14 g (0.06 mol) of crude 1-benzyl-4-chloromethyl-pyrrolidin-2-one, prepared as in Example 1(a), 10 g of diethylamine and 50 ml of dimethylformamide are stirred or shaken for 2 hours at 150° C. in the autoclave. The mixture is evaporated to dryness in vacuo and the residue is taken up in methylene chloride then washed first with water and finally the title compound is extracted twice with 25 ml of 2 NHCl. The aqueous phase is removed, made alkaline with sodium hydroxide solution and the organic base is extracted with methylene chloride. The methylene chloride phase is concentrated by evaporation and the residue is distilled in vacuo.

Yield: 10 g (61% of theory), bp$_{0.05}$ = 155°–158° C.

EXAMPLE 6

(−)-1-Benzyl-4-diethylaminomethyl-pyrrolidin-2-one 11.5 g (0.056 mol) of (−)-1-benzyl-4-aminomethyl-pyrrolidin-2-one, 130 ml of water, 13 g of acetaldehyde, 5.8 ml of concentrated hydrochloric acid and 6.5 g of Pd C 20% are hydrogenated for 5¼ hours at 5 bar and at 25° C. The residue is evaporated, taken in 30 ml of water and extracted with methylene chloride. The aqueous hydrochloric acid solution is made alkaline and also extracted with methylene chloride. By distillation in a bulbed tube, 11.2 g (76.4% of theory) of the title compound are obtained, $\alpha_D = -9.4$ (c=1.0; methanol). Analogously to Example 6, by hydrogenating 8.4 g (0.041 mol) of (+)-1-benzyl-4-aminomethyl-pyrrolidin-2-one, 95 ml of water, 9.5 acetaldehyde, 4.2 ml of concentrated hydrochloric acid and 4.7 g of Pd/C 20%. (+)-1-benzyl-4-diethylaminomethyl-pyrrolidin-2-one is obtained, $\alpha_D = +9.4$ (c=1.0; methanol).

EXAMPLE 7

1-(4-Fluoro-benzyl)-4-N-methylpiperazinylmethyl-pyrrolidin-2-one (a) 24 g (0.11 mol) of 1-(4-fluorobenzyl)-4-hydroxymethyl-pyrrolidin-2-one are refluxed with 10 ml (0.14 mol) of thionyl chloride in 200 ml of methylene chloride first of all for 10 hours and then, after the addition of another 10 ml of thionyl chloride, for a further 6 hours. Whilst cooling with ice, the product is neutralised with ammonia and after the organic phase has been separated off it is dried and concentrated by evaporation. 23 g (92% of theory) of a reddish-brown oil remain, which is used without any further purification.

(b) 5 g (0.002 mol) of the above oil are refluxed for 1-2 hours with 4.4 g (0.04 mol) of 1-methyl-piperazine in 30 ml of dimethylformamide. The dimethylformamide is then substantially distilled off in vacuo, the residue is taken up in methylene chloride and washed with water and then the organic phase is dried and evaporated again. The residue is chromatographed on SiO$_2$ with methylene chloride/methanol 95:5 as eluant. The main fraction is concentrated by evaporation and the residue (5 g) is dissolved in 30 ml of methanol. 2.8 g of fumaric acid are added to this solution. 5.2 g (48% of theory) of the title compound are precipitated in crystalline form as the fumarate.

M.p. 179°–180° C.

EXAMPLE 8

1-(4-Fluorobenzyl)-4-morpholinomethyl-pyrrolidin-2-one (a) 8.9 g (0.04 mol) of 1-(4-fluorobenzyl)-4-hydroxymethyl-pyrrolidin-2-one in 100 ml of absolute methylene chloride and 4.8 g of pyridine are mixed with 6.9 g (0.06 mol) of methanesulphonic acid chloride. The mixture is refluxed for 2.5 hours then cooled and extracted with dilute ammonia and water. The organic phase is dried and concentrated by evaporation. 11 g (93% of theory) of crude ester are obtained, m.p. 84°–86° C.

(b) 6.7 g (0.023 mol) of ester and 2.6 g (0.03 mol) of morpholine are refluxed for 2 hours in 20 ml of dioxan. The solvent is evaporated off in vacuo and the residue is taken up in methylene chloride and extracted with 50 ml of 2N hydrochloric acid. The aqueous extracts are made alkaline with ammonia and the oily base is extracted with methylene chloride. The methylene chloride phase is dried and concentrated by evaporation. The residue (4.2 g) is taken up in 30 ml of methanol and 1.2 g of fumaric acid are added in the warm. After cooling, the fumarate of the title compound is precipitated in crystalline form.

Yield: 7 g=57% of theory of colourless crystals, m.p. 175°–176° C.

EXAMPLE 9

1-(4-Fluorobenzyl)-4-amino-pyrrolidin-2-one (a) 4.0 g (0.013 mol) of mesyl ester, prepared according to Example 7, are refluxed for 30 minutes with 2.8 g (0.015 mol) of phthalimide potassium in 50 ml of dimethylformamide. The mixture is concentrated by evaporation in vacuo and the residue is taken up in methylene chloride, washed with water, the organic phase is dried and again concentrated by evaporation. The residue is triturated with ether and yields 3.6 g (78% of theory) of light grey crystals, m.p. 124°–125° C.

(b) 3.5 g (0.1 mol) of the above phthalimide compound are stirred with 5.5 g of hydrazine hydrate in 200 ml of alcohol for 4 hours at ambient temperature. The mixture is worked up as described in Example 1. 2.5 g (89% of theory) of the fumarate of the title compound are obtained, m.p. 214°–215° C.

The title compound may also be obtained by dissolving 5 g (16 mmol) of mesyl ester (see Example 7) in 100 ml of dimethylformamide and, after the addition of 1.3 g of sodium azide, heating the mixture to 100° C. for 2 hours, hydrogenating the oil which is obtained in due course with Raney nickel in methanol and converting the base into the fumarate as described above.

Yield: 4.2 g (90% of theory).

The following end products were also obtained analogously to the procedure described in the above Examples:

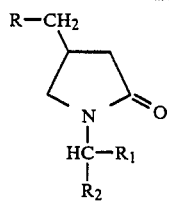

| Example No. | R | $R_1$ | $R_2$ | Mp. °C./Bp. °C. |
|---|---|---|---|---|
| 10 | $-NH_2$ | H | ⌬-$OCH_3$ (para) | Mp. 215–216 (Fumarate) |
| 11 | $-NH_2$ | H | ⌬-$OCH_3$, $OCH_3$ (3,4-dimethoxyphenyl) | Mp. 187–189 (Fumarate) |
| 12 | $-NH_2$ | H | ⌬-$CH_3$ (para) | Mp. 225–226 (Fumarate) |
| 13 | $-NH_2$ | H | ⌬-Cl (para) | Mp. 189–191 (Fumarate) |
| 14 | $-NH_2$ | H | ⌬-$CF_3$ (meta) | Mp. 168–169 (Fumarate) |
| 15 | $-NH_2$ | H | 4-pyridyl | Mp. 179–181 (Fumarate) |
| 16 | $-NH_2$ | $-CH_3$ | ⌬-$OCH_3$ (para) | Mp. 167–168 (Fumarate) |
| 17 | piperidin-1-yl | H | phenyl | Mp. 58–60<br>Bp.$_{0.05}$ 180 (Base) |
| 18 | 4-methylpiperazin-1-yl | H | phenyl | Mp. 190–192 (Fumarate) |
| 19 | imidazol-1-yl | H | phenyl | Bp.$_{0.05}$ 230 (Base) |
| 20 | $-HN-CH_3$ | H | phenyl | Bp.$_{0.05}$ 180 (Base) |

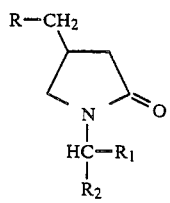

| Example No. | R | $R_1$ | $R_2$ | Mp. °C./Bp. °C. |
|---|---|---|---|---|
| 21 | —$NH_2$ | H | 2-Cl-phenyl | Mp. 179–180 (Fumarate) |
| 22 | —N($C_2H_5$)$_2$ | H | 2-Cl-phenyl | Bp.$_{0.05}$ 156 (Base) |
| 23 | —NH—CH(CH$_3$)$_2$ | H | phenyl | Bp.$_{0.05}$ 175 (Base) |
| 24 | —N($C_2H_5$)$_2$ | H | 4-CH$_3$-phenyl | Bp.$_{0.05}$ 175 (Base) |

EXAMPLE 25

1-Benzyl-5-dimethylaminomethyl-pyrrolidin-2-one (a) A solution of 10.26 g (0.05 mol) of 1-benzyl-5-hydroxymethyl-pyrrolidin-2-one (m.p. 76°–77° C.) and 5.6 g (0.055 mol) of triethylamine in 80 ml of methylene chloride is mixed with 6.3 g (0.055 mol) of methanesulphonic acid chloride in 20 ml of methylene chloride. The reaction mixture is then refluxed for 1 hour and, after being cooled, extracted with water. The organic phase is dried over anhydrous sodium sulphate and then concentrated by evaporation in a rotary evaporator. 14.1 g (yellow oil) of crude 1-benzyl-5-hydroxymethyl-pyrrolidin-2-one methanesulphonic acid ester is obtained, which is used in the next reaction step without any further purification.

(b) 8.5 g (0.03 mol) of the mesylate obtained in (a) are heated to 150° C. for 3 hours with a solution of 10 g of dimethylamine in 60 ml of dioxan in an autoclave. After cooling the reaction mixture is concentrated to dryness in vacuo. The residue is dissolved in 2N hydrochloric acid and extracted with ether. The acidic aqueous phase is made alkaline with concentrated ammonia and extracted with methylene chloride. The methylene chloride solution is dried and concentrated by evaporation. The residue (6.5 g) is converted into the acid fumarate of the title compound with an equivalent amount of fumaric acid. Yield: 6.4 g (61% of theory); m.p. 137°–138° C.

The following were also prepared analogously to Example 25:

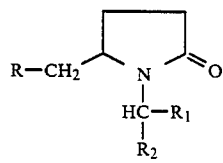

| Example No. | R | $R_1$ | $R_2$ | Mp. °C./Bp. °C. |
|---|---|---|---|---|
| 26 | —N($C_2H_5$)$_2$ | H | phenyl | Mp. 163–164 (Hydrochloride) |

-continued

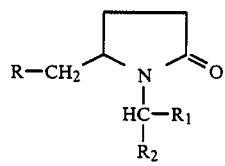

| Example No. | R | $R_1$ | $R_2$ | Mp. °C./Bp. °C. |
|---|---|---|---|---|
| 27 | —N(morpholino) | H | phenyl | Mp. 167–169 (Oxalate) |
| 28 | —N(4-methylpiperazinyl) | H | phenyl | Mp. 258 (Dihydrochloride) |
| 29 | —N(pyrrolidinyl) | H | phenyl | Mp. 188–190 (Hydrochloride) |
| 30 | —N(CH$_3$)$_2$ | H | 4-CH$_3$-phenyl | Mp. 163–164 (Fumarate) |
| 31 | —N(C$_2$H$_5$)$_2$ | H | 4-CH$_3$-phenyl | Mp. 152–153 (Hydrochloride) |
| 32 | —N(CH$_3$)$_2$ | H | 4-Cl-phenyl | Mp. 157–158 (Fumarate) |
| 33 | —N(C$_2$H$_5$)$_2$ | H | 4-Cl-phenyl | Mp. 149–151 (Hydrochloride) |
| 34 | —N(CH$_3$)$_2$ | H | 3,4-diCl-phenyl | Mp. 167–168 (Fumarate) |
| 35 | —N(C$_2$H$_5$)$_2$ | H | 3,4-diCl-phenyl | Mp. 159–161 (Hydrochloride) |
| 36 | —N(CH$_3$)$_2$ | H | 4-OCH$_3$-phenyl | Oil (Base) |
| 37 | —N(C$_2$H$_5$)$_2$ | H | 4-OCH$_3$-phenyl | Oil (Base) |

EXAMPLE 38

1-Benzyl-5-aminomethyl-pyrrolidin-2-one 16.4 g (0.07 mol) of 1-benzyl-5-hydroxymethyl-pyrrolidin-2-one methanesulphonic acid ester (see Example 25 (a)) are dissolved in 200 ml of dimethylformamide and stirred for 90 minutes at 100° C. after the addition of 4.6 g (0.07 mol) of sodium azide. After evaporation, distributing between water and methylene chloride and working up of the organic phase, 13.8 g (92% of theory) of oil are obtained, which can be reacted further in its crude form. It is dissolved in 200 ml of methanol and, after the addition of Raney nickel, hydrogenated at 20° C. and 5 bar. After the catalyst has been removed by suction filtering and the filtrate has been evaporated, 11 g (85% of theory) of oil are obtained which when dissolved in methanol and after the addition of fumaric acid yields the desired hemifumarate of the title compound (m.p. 187°–188° C.).

Pharmaceutical formulation Examples

| (A) Tablets | per tablet |
|---|---|
| Active substance | 100 mg |
| Lactose (powdered) | 140 mg |
| Corn starch | 240 mg |
| Polyvinylpyrrolidone | 15 mg |
| Magnesium stearate | 5 mg |
| | 500 mg |

The finely ground active ingredient, lactose and part of the corn starch are mixed together. The mixture is screened and then moistened with a solution of polyvinylpyrrolidone in water, kneaded, granulated whilst moist and then dried. The granulate, the remaining corn starch and the magnesium stearate are screened and mixed together. The mixture is compressed to form tablets of suitable shape and size.

| (B) Tablets | per tablet |
|---|---|
| Active substance | 80 mg |
| Corn starch | 190 mg |
| Lactose | 55 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture is screened and processed with the remaining corn starch and water to form a granulate which is dried and screened. The sodium carboxymethyl starch and the magnesium stearate are added and the mixture is compressed to form tablets of suitable size.

| (C) Ampoules | |
|---|---|
| 1-Benzyl-4-aminomethyl-pyrrolidin-2-one fumarate | 50.0 mg |
| Sodium chloride | 10.0 mg |
| Doubly distilled water q.s. ad | 1.0 ml |

Method

The active substance and sodium chloride are dissolved in doubly distilled water and the solution is transferred into ampoules under sterile conditions.

| (D) Drops | |
|---|---|
| 1-Benzyl-4-aminomethyl-pyrrolidin-2-one fumarate | 5.0 g |
| methyl p-hydroxybenzoate | 0.1 g |
| propyl p-hydroxybenzoate | 0.1 g |
| demineralised water q.s. ad | 100.0 ml |

Method

The active substance and preservatives are dissolved in demineralised water and the solution is filtered and transferred into vials each containing 100 ml.

What is claimed is:

1. A method of treating depression which comprises administering, to a human host suffering from depression an antidepressive amount of a compound of the formula I

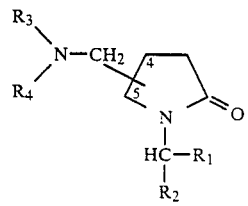

wherein $R_1$ represents hydrogen or a $C_2$–$C_4$ alkyl group, $R_2$ represents a phenyl group which may be mono- or disubstituted by $C_1$–$C_2$ alkoxy, fluorine, chlorine, bromine trifluoromethyl, $C_1$–$C_4$ alkyl, hydroxy or nitro, or $R_2$ represents a pyridyl group, and $R_3$ and $R_4$ together with the nitrogen atom represent a group of the formula

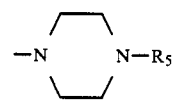

wherein $R_5$ is H or methyl, or a pharmaceutically acceptable acid addition salt thereof.

* * * * *